United States Patent
Takagi

(10) Patent No.: US 9,662,138 B2
(45) Date of Patent: May 30, 2017

(54) PUNCTURE CONTROL SYSTEM AND METHOD THEREFOR

(71) Applicant: CANON KABUSHIKI KAISHA, Tokyo (JP)

(72) Inventor: Kiyoshi Takagi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/411,074

(22) PCT Filed: Jun. 11, 2013

(86) PCT No.: PCT/JP2013/066539
§ 371 (c)(1),
(2) Date: Dec. 23, 2014

(87) PCT Pub. No.: WO2014/002805
PCT Pub. Date: Jan. 3, 2014

(65) Prior Publication Data
US 2015/0150591 A1 Jun. 4, 2015

(30) Foreign Application Priority Data
Jun. 26, 2012 (JP) ................. 2012-142961

(51) Int. Cl.
*G06F 19/00* (2011.01)
*A61B 17/34* (2006.01)
(Continued)

(52) U.S. Cl.
CPC .... *A61B 17/3403* (2013.01); *A61B 17/00234* (2013.01); *A61B 34/10* (2016.02);
(Continued)

(58) Field of Classification Search
CPC ..... A61B 17/3478; A61B 19/22; A61B 19/52; A61B 19/5244; A61B 19/2203; A61B 19/50; A61B 17/00234; A61B 17/3403
(Continued)

(56) References Cited

U.S. PATENT DOCUMENTS 8,282,565 B2 * 10/2012 Mahapatra ........... A61B 5/4887
600/486
8,348,861 B2 * 1/2013 Glozman ........... A61B 17/3478
600/407
(Continued)

FOREIGN PATENT DOCUMENTS

EP 1905377 A1 4/2008
JP 2006271546 A 10/2006
(Continued)

OTHER PUBLICATIONS

Daniel Glozman et al., Flexible Needle Steering an Optimal Trajectory Planning for Percutaneous Therapies, Jan. 1, 2004, pp. 137-144.

*Primary Examiner* — Jaime Figueroa
(74) *Attorney, Agent, or Firm* — Canon U.S.A. Inc., IP Division

(57) ABSTRACT

The puncture control system includes a trajectory error compensation filter for outputting a control signal for compensating for the error of a puncture needle from a target trajectory based on information on the position of the puncture needle obtained by a detector, a displacement compensation filter for which initial control parameters are determined based on a model representing characteristics of an organ, and an adder for outputting an added signal obtained by adding outputs of the trajectory error compensation filter and the displacement compensation filter. The organ model is used to predict a displacement of a puncture (Continued)

target position and sequentially determine a course of the puncture needle.

18 Claims, 7 Drawing Sheets

(51) Int. Cl.
  *A61B 17/00*   (2006.01)
  *A61B 34/30*   (2016.01)
  *A61B 34/10*   (2016.01)
  *A61B 34/20*   (2016.01)
  *A61B 90/00*   (2016.01)

(52) U.S. Cl.
  CPC .............. *A61B 34/30* (2016.02); *A61B 34/20* (2016.02); *A61B 90/37* (2016.02); *A61B 2034/105* (2016.02); *A61B 2034/107* (2016.02)

(58) Field of Classification Search
  USPC ............... 700/245, 257, 258, 260, 261, 264; 606/130; 600/407, 585, 587
  See application file for complete search history.

(56) References Cited

U.S. PATENT DOCUMENTS

| | | | |
|---|---|---|---|
| 2006/0095022 A1* | 5/2006 | Moll | A61B 8/12 606/1 |
| 2007/0016067 A1 | 1/2007 | Webster et al. | |
| 2008/0082110 A1* | 4/2008 | Rodriguez Ponce | A61B 19/52 606/130 |
| 2009/0149867 A1* | 6/2009 | Glozman | A61B 17/3478 606/130 |
| 2010/0312129 A1* | 12/2010 | Schecter | A61B 5/0031 600/508 |
| 2011/0270270 A1 | 11/2011 | Vancamberg et al. | |
| 2012/0130218 A1* | 5/2012 | Kauphusman | A61B 5/0422 600/373 |
| 2012/0265051 A1* | 10/2012 | Fischer | A61B 10/0241 600/411 |

FOREIGN PATENT DOCUMENTS

| | | |
|---|---|---|
| JP | 2008237783 A | 10/2008 |
| JP | 2010506600 A | 3/2010 |
| WO | 2007141784 A2 | 12/2007 |

\* cited by examiner

PUNCTURE CONTROL SYSTEM AND METHOD THEREFOR

TECHNICAL FIELD

The present invention relates to a puncture control system using robot technologies and to a method for the puncture control system.

BACKGROUND ART

Minimum-invasive treatment are effective therapy methods that place less physical burden on patients and allow reductions in medical treatments after a surgery and in rehabilitation period. As methods of minimum-invasive percutaneous treatment, local therapies in which a puncture needle is directly led to a tumor tissue in an organ to necrotize the tumor tissue by a radio wave, microwave, laser, or the like have been attracting attention. There is also known a puncture system in which a puncture needle is inserted to a skin while a position of a tumor is confirmed by equipment such as ultrasound, CT, or MRI so as to allow confirmation that the needle has reached inside the tumor.

In a puncture control system, it is required that a tip of the puncture needle accurately reach a puncture target position (for example, tumor tissue) in a tissue of an organ. However, a puncture operation requires skill and trial and error of a doctor because a puncture error is generated, and is difficult even with image guidance. The puncture error includes, for example, a target trajectory error and a target displacement error.

The target trajectory error is an error in which the puncture needle itself deforms with a resistance while traveling through the tissue of the organ, and because the deformation is not uniform due to unevenness of the tissue in a puncture route, a direction of travel of the needle is displaced. The target displacement error is an error that is generated because a target position is moved when, while the needle travels through the tissue of the organ, the tissue of the organ is deformed by a force imparted to the organ by the needle or the tissue is deformed with a change in direction of gravitational force with respect to a posture of the patient.

Such puncture error leads to a problem in that the tip of the puncture needle does not accurately reach the puncture target position in the tissue of the organ, or in which the route through which the needle reaches the puncture target position greatly differs from a planned route because the puncture target position is moved.

In the conventional puncture control system, the puncture error in which the puncture target position is displaced when, while correcting a course of the needle, the force of the tip of the needle is transferred to the puncture target position through the tissue of the organ has not been considered. Therefore, there are known a system and a method in which the course correction is performed every time the puncture target position is displaced.

PTL 1 discloses a puncture control system for correcting various kinds of information (general information) of the general human liver to individual information corresponding to the individual difference of a puncture object patient. The puncture control system combines information by a model obtained from the individual information with force information and visual information obtained by a force sensor and an image acquisition device to decide a course of a needle, and gives a drive command to an actuator.

CITATION LIST

Patent Literature

PTL 1: Japanese Patent Application Laid-Open No. 2006-271546

SUMMARY OF INVENTION

Technical Problem

FIG. 9A is a schematic diagram conceptually illustrating a process in which a puncture needle reaches a target position based on the disclosure of PTL 1.

First, a needle 21 is inserted to an organ O and toward a position T1 of the target position, which is confirmed in a state in which the needle 21 has not entered the organ. When the needle 21 is inserted to the organ O and travels therethrough (P1), the organ is deformed by the force imparted to an outer wall of the organ at the time of insertion and the force with which the needle 21 enters and travels through the organ to displace the target position from the position T1 to a position T2.

To adapt to the displacement, in the subsequent control step, a course of the needle is changed to P2 toward the moved target position T2. Then, due to the deformation of the organ caused by a pressing force of the needle 21 in its travel, the position T2 of the target position changes to a position T3, and due to this movement, the course of the needle 21 is changed to P3. Thereafter, in a similar manner, when the course of the needle 21 is changed to P3, the position T3 of the target position changes to a position T4, and when the course of the needle 21 is changed to P4, the position T4 of the target position changes to a position T5.

As described above, in the conventional course correction method, the actual displacement of the puncture target position is recognized in the image obtained in the next control step and the course of the needle is corrected again. In this method, the course correction of the needle allows the displacement of the puncture target position, and the course of the needle always follows the displacement. As a result, the course vibrates or convergence takes time, which leads to a problem in that a normal tissue is damaged or the final puncture accuracy is not improved.

Solution to Problem

An object of the present invention is to provide a puncture control system for use in an organ puncture system, the organ puncture system including: a puncture needle for which a control force and a control torque are controlled by a manipulator and which moves toward a target position of an organ; a detector for obtaining information on a position of the puncture needle; and an image obtaining unit for obtaining information on the organ that changes with travel of the puncture needle through the organ, the puncture control system inputting a signal for controlling a position of a tip of the puncture needle to the manipulator, the puncture control system including: a trajectory error compensation filter for outputting, based on the information on the position of the puncture needle obtained by the detector, a signal for compensating for a displacement of the puncture needle from a target trajectory; a displacement compensation filter for which initial control parameters are determined so as to correspond to a model representing characteristics of the organ; and an adder for outputting a signal obtained by adding the signal output by the trajectory error compensation filter and the signal output by the displacement compensation filter.

Further features of the present invention will become apparent from the following description of exemplary embodiments with reference to the attached drawings.

DESCRIPTION OF EMBODIMENT

Preferred embodiments of the present invention will now be described in detail in accordance with the accompanying drawings.

Next referring to FIGS. 1 to 7, a puncture control system according to the present invention and an organ puncture system including the puncture control system are described.

Figure 1:
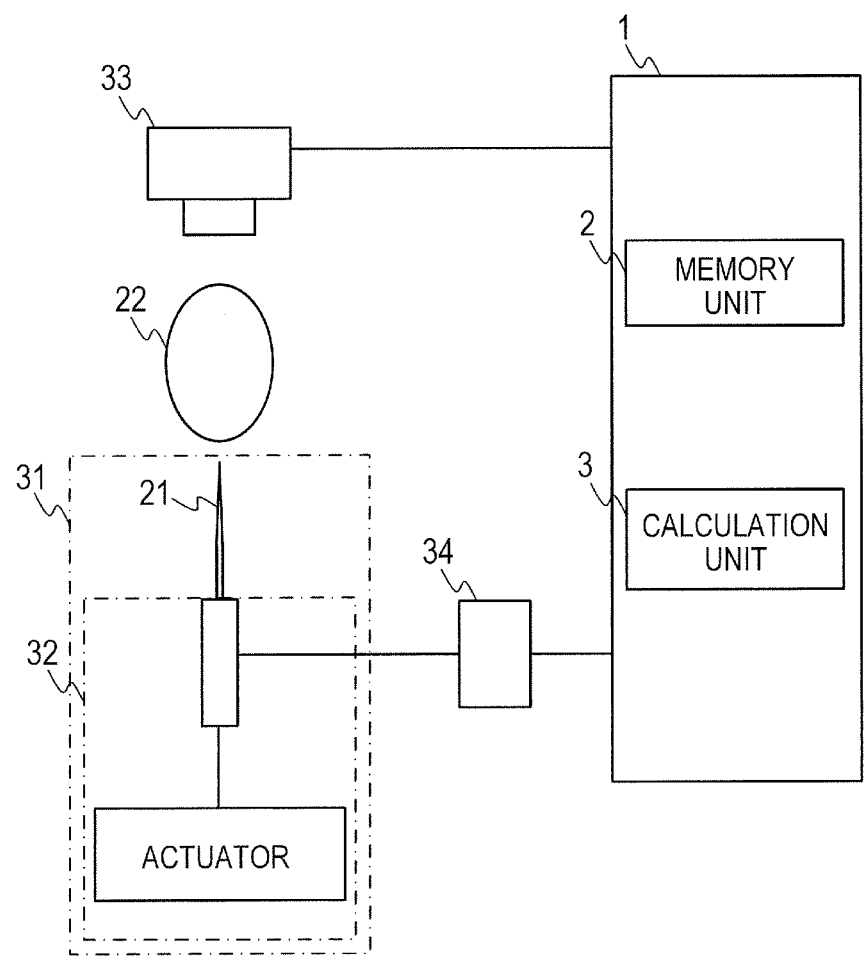
FIG. 1 is a block diagram illustrating a configuration of an organ puncture system according to the present invention.

FIG. 1 is a schematic diagram illustrating a configuration of the organ puncture system. The organ puncture system includes a puncture control system 1, a needle robot 31, an image obtaining unit 33, and a detector 34. The puncture control system 1 includes a memory unit 2 and a calculation unit 3. The needle robot 31 includes a puncture needle 21 and an articulated manipulator 32 including an actuator. The manipulator 32 holds the puncture needle 21 at its tip. The puncture control system 1 performs, in a control model stored in the memory unit 2, revision of control input and control parameters of a model and the like by the calculation unit 3 to output a signal for controlling a position of the tip of the puncture needle 21 to the manipulator 32.

The image obtaining unit 33 obtains information on the organ that changes with the travel of the puncture needle 21 in the organ. The detector 34 may obtain the information on the puncture needle 21 that changes momentarily as an image. The information on the organ that is obtained as the image includes how the organ is deformed and information on a position of a target position of the puncture needle 21. The information on the organ may also be obtained from an angle sensor.

Figure 2:
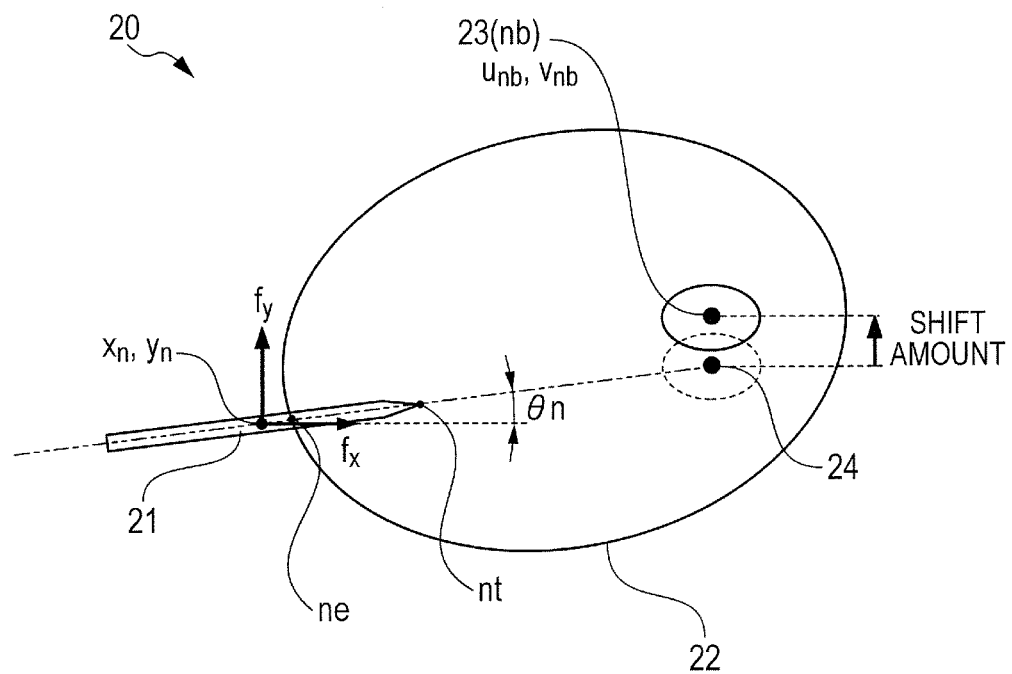
FIG. 2 is an explanatory diagram illustrating a relationship between a puncture needle and a target position of an organ according to the present invention.

FIG. 2 illustrates a concept of simultaneous control of a trajectory of the puncture needle 21 and a change in position of a puncture target position. The organ may be expressed by a finite element model having arbitrary numbers of elements and nodes. It is assumed that the puncture needle 21 has entered an organ model 22 from an ne-th node and its tip has reached an nt-th node. The puncture needle 21 travels toward a position 24 of the target position at an nb-th node. However, due to a pressing force of the puncture needle 21, the actual nb-th node of the target position moves from the position 24 to a position 23 by a shift amount. The shift amount is obtained as shifts $u_{nb}$ and $v_{nb}$ by the image obtaining unit 33. The position of the tip of the puncture needle 21 is detected and obtained by the detector 34.

The present invention is intended to suppress the change in position of the puncture target position. Therefore, characteristics of the organ model 22 need to be captured along with characteristics of the needle robot 31. For that purpose, the organ model 22 is included in the model of the needle robot 31 stored in the memory unit of the puncture control system 1 as follows to be modeled as an extended system 25.

1) Modeling

Mass and a moment of inertia about the center of gravity of the puncture needle 21 of the needle robot 31 are represented by $m_n$ and $J_n$, respectively. It is assumed that to shifts $x_n$ and $y_n$ of the center of gravity and a rotation angle $\theta_n$ of the puncture needle 21, a control force $f_x$ in an x direction and a control force $f_y$ in a y direction, which are imparted to the puncture needle 21, and a control torque $t_n$ about the center of gravity are arbitrarily applied, respectively. In this case, an equation of motion of the puncture needle 21 is expressed by Equation (1).

$$M_n \ddot{q} = u, \quad M_n = \begin{bmatrix} m_n & 0 & 0 \\ 0 & m_n & 0 \\ 0 & 0 & J_n \end{bmatrix}, \quad q = \begin{bmatrix} x_n \\ y_n \\ \theta_n \end{bmatrix}, \quad u = \begin{bmatrix} f_x \\ f_y \\ t_\theta \end{bmatrix} \quad (1)$$

When it is assumed here that $$x = [q \, \dot{q}]^T$$

an equation of state and an output equation of the needle robot are expressed by Equations (2) and (3).

$$\dot{x} = A_n x + B_n u \quad (2)$$

$$y = C_n x \quad (3)$$

Next, it is assumed that the organ model 22 is a finite element model having the number of elements m and the number of nodes n. To the nodes divided by the finite elements, a stiffness parameter, a mass parameter, and an attenuation parameter are distributed. Characteristics of the organ are represented by a stiffness matrix K, a mass matrix M, and an attenuation matrix C. The attenuation matrix C corresponds to attenuation amounts of the forces that have acted on the organ. When shifts in the x and y directions of an n-th node are represented by $u_n$ and $v_n$ and node forces that act are represented by $f_{xn}$ and $f_{yn}$, a node displacement vector $\delta$ and a node force vector $f$ as a whole may be expressed as follows.

$$\delta = [u_1 v_1 \ldots u_n v_n]^T, f = [f_{x1} f_{y1} \ldots f_{xn} f_{yn}]^T$$

When the vectors are used, the equation of motion is expressed by Equation (4) below.

$$M\ddot{\delta} + C(\delta, \dot{\delta})\dot{\delta} + K(\delta, \dot{\delta})\delta = f \quad (4)$$

The second and third terms of Equation (4) indicate that the organ model 22 is a non-linear system in which stiffness and attenuation vary depending on shifts of the nodes.

When it is assumed that the force of the tip of the puncture needle 21 of the needle robot 31 is applied only on the nt-th node of the organ model 22, a node force f is expressed in matrix form by Equation (5).

$$f = \begin{bmatrix} 0_{2(nt-1)\times 1} & 0_{2(nt-1)\times 1} & 0_{2(nt-1)\times 1} \\ 1 & 0 & -l\sin\theta_n \\ 0 & 1 & l\cos\theta_n \\ 0 & 0 & 0 \\ \vdots & \vdots & \vdots \\ 0 & 0 & 0 \end{bmatrix} \begin{bmatrix} f_x \\ f_y \\ t_\theta \end{bmatrix} = F(q)u \quad (5)$$

When it is assumed here that $$x_o = [\delta \dot{\delta}]^T,$$

an equation of state of the organ model 22 can be written as Equation (6).

$$\dot{x}_o = \begin{bmatrix} 0 & I \\ -M^{-1}K(\delta, \dot{\delta}) & -M^{-1}C(\delta, \dot{\delta}) \end{bmatrix} x_o + \begin{bmatrix} 0 \\ M^{-1}F \end{bmatrix} \quad (6)$$

$$u = A_o(x_o)x_o + B_o(q, x_o)u$$

Further, when it is assumed that the nb-th node is the puncture target position and that the shifts $u_{nb}$ and $v_{nb}$ thereof may be observed by an image obtaining unit such as MRI, the output equation may be written as Equation (7).

$$y_o = \begin{bmatrix} 0_{1\times 2(nb-1)} & 1 & 0 & 0 & \ldots & 0 \\ 0_{1\times 2(nb-1)} & 0 & 1 & 0 & \ldots & 0 \end{bmatrix} x_o = C_o x_o \quad (7)$$

Next, when a state of the extended system 25 of the needle robot and the organ model 22 is set as follows:

$$x_w = [x x_o]^T,$$

an equation of state and an output equation of the extended system 25 are expressed by Equations (8) and (9), respectively.

$$\dot{x}_w = \begin{bmatrix} A_n & 0 \\ 0 & A_o(x_o) \end{bmatrix} x_w + \begin{bmatrix} B_n \\ B_o(q, x_o) \end{bmatrix} \quad (8)$$

$$u = A_w(x_w)x_w + B_w(x_w)u$$

$$y_w = \begin{bmatrix} C_n & 0 \\ 0 & C_o \end{bmatrix} x_w = C_w x_w \quad (9)$$

Based on Equation (8), the control input to the needle robot 31 becomes an input that allows, while changing the organ model 22, the needle robot 31 (actuator of manipulator 32) to be driven. In other words, through suitable determination of the control input, the shifts of the puncture needle 21 of the needle robot 31 and the shifts of the position 23 of the puncture target position in the organ model 22 may be adjusted simultaneously. A method of deriving the control input is described next.

Figure 3:
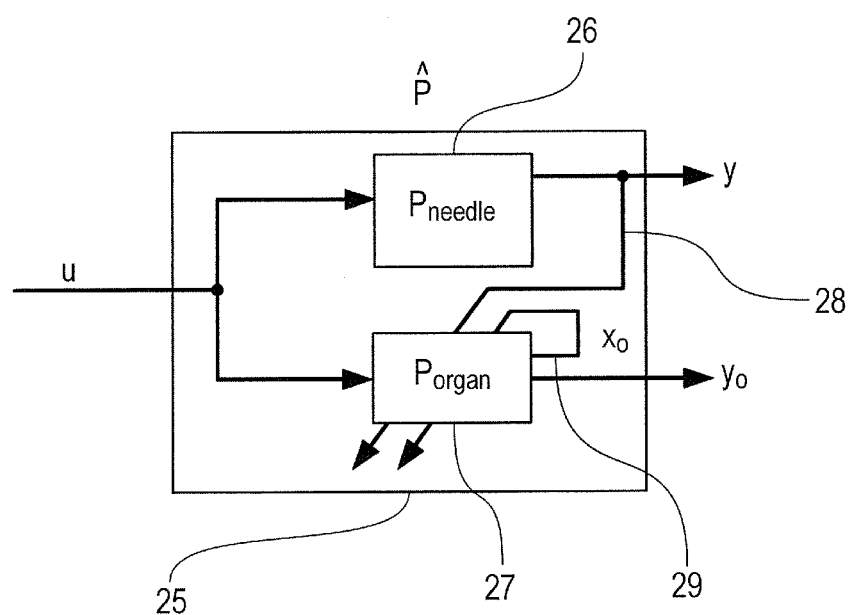
FIG. 3 is a block diagram illustrating an extended system according to the present invention.

FIG. 3 is a block diagram of the extended system 25. The model of the extended system 25 is the model expressed by Equation (8). The extended system 25 includes a block 26 of the needle robot 31 expressed by Equation (2) and a block 27 of the organ model 22 expressed by Equation (6). Through a signal path 28, the node to which the forces are applied in the organ model 22 is changed by an output of the block 26. Further, by a signal that passes through a signal path 29, the stiffness matrix K, the mass matrix M, and the attenuation matrix C of the organ model 22 in the block 27 are revised.

2) Control System of Puncture Control System

First, a target trajectory through which the tip of the puncture needle 21 of the needle robot 31 reaches the position 24 of the puncture target position is set. Then, a control system is designed so that while the needle robot 31 follows the target trajectory, the displacement of the position 24 of the puncture target position is minimized. In this embodiment, a feedback control system is designed by using an H∞ control system, but may be designed by using an optimal control system or a model predictive control system.

Figure 4:
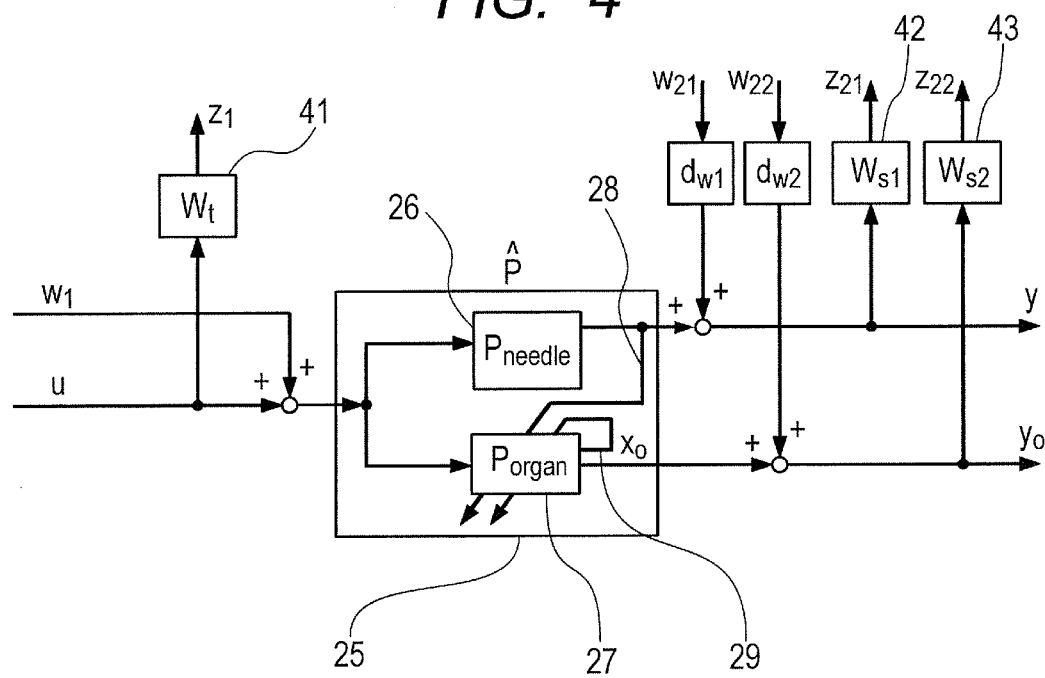
FIG. 4 is a block diagram illustrating a generalized plant according to the present invention.

First, a plant model that is generalized for designing the H∞ control system is prepared. FIG. 4 illustrates the plant model. In the figure, $w_1$, $w_{21}$, and $w_{22}$ are external inputs, $z_1$, $z_{21}$, and $z_{22}$ are control amounts, and filters 41, 42, and 43 are filters that use weighting functions $W_t$, $W_{s1}$, and $W_{s2}$. In particular, $z_{21}$ and $z_{22}$ are control amounts for a trajectory following performance of the robot and the shifts of the puncture target position, respectively. The weighting functions are designed and the control amounts $z_{21}$ and $z_{22}$ from the external input $w_1$ are evaluated, to thereby realize minimization of a trajectory following error and the displacement of the puncture target position simultaneously. The control system to be designed takes connection to the plant model (in practice, real plant) into consideration, and is designed so as to input y and $y_o$ and output a control input u. When a transfer function of a closed-loop system including the plant model from an external input $w_n$ to a control amount $z_m$ and the control system is denoted by $G_{zmwn}$, the H∞ control system is designed using an evaluation function expressed by Equation (10) below.

$$\left\| \begin{matrix} G_{z22w1} \\ G_{z21w1} \end{matrix} \right\|_\infty < \gamma \quad (10)$$

In the expression, $G_{z21w1}$ represents a transfer function obtained by multiplying a setting function from the control input u to a position y of the tip of the puncture needle 21 of the needle robot 31 by the weighting function $W_{s1}$. A control system that minimizes an ∞ norm of the transfer function is determined to realize the trajectory following by the needle robot. Similarly, $G_{z22w1}$ represents a transfer function obtained by multiplying a setting function from the control input u to a puncture target position $y_o$ by the weighting function $W_{s2}$. A control system that minimizes an ∞ norm is determined so that the displacement of the puncture target position may be suppressed by the control input of the needle robot. $G_{z21w1}$ and $G_{z22w1}$ are evaluated simultaneously by Equation (10) to derive a control system that controls the trajectory following and the shifts of the puncture target position simultaneously. In Equation (10), the control system is determined so that γ is a positive number and takes as small a value as possible. Note that, when a model error and the like are taken into consideration, all evaluation paths $G_{z1w1}$ may be used. The control system is realized by the following equation of state. In the equation, $x_k$ is a state of the control system.

$$\dot{x}_k = A_k x_k + B_k y_w \quad (11)$$

$$u = C_k x_k + D_k y_w \quad (12)$$

Figure 5:
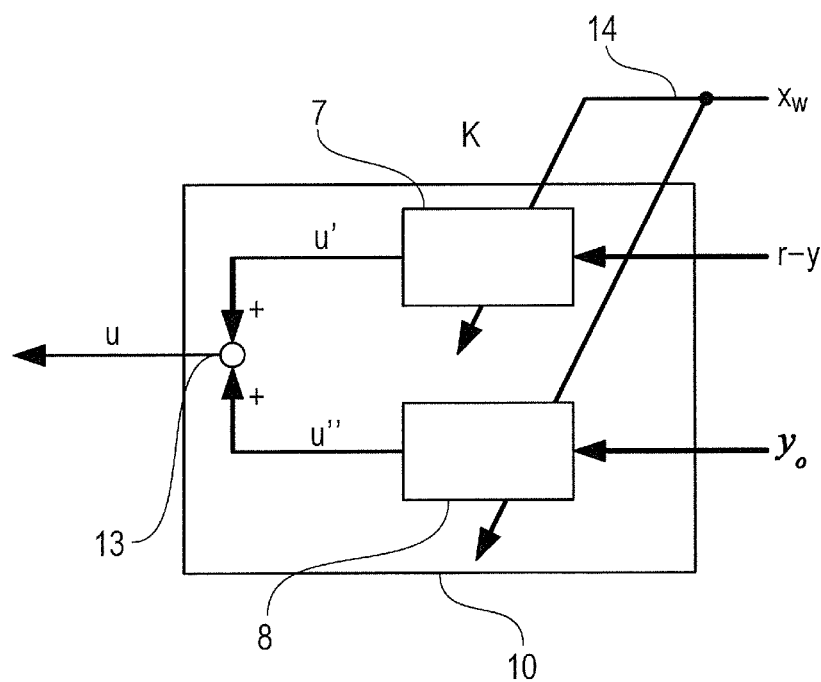
FIG. 5 is a block diagram illustrating a control system according to the present invention.

FIG. 5 is a block diagram of a designed control system 10. The control system 10 corresponds to the equation of state and the output equation expressed by Equations (11) and (12). The control system 10 includes a trajectory error compensation block 7, a displacement compensation block 8, and an adder 13. First, a difference signal input (r−y) representing a difference between a position r of the target trajectory and the actual position y of the puncture needle 21 is input to the trajectory error compensation block 7 so that a signal of the position y of the puncture needle 21 approaches the position r of the target trajectory. Then, the trajectory error compensation block 7 generates and outputs a trajectory compensation signal u' so that the difference signal input (r−y) is reduced, the trajectory compensation signal u' being a control input that compensates for the trajectory following error of the needle robot 31 corresponding to the position of the puncture needle 21. Moreover, control parameters of the trajectory error compensation block 7 are revised so that the state $x_w$ of the real plant that changes with the position y of the puncture needle 21 represents actual characteristics of the organ in a state in which the puncture needle 21 is traveling through the organ. The trajectory error compensation block 7 having the revised control parameters may generate and output the trajectory compensation signal u' so as to suit the state—$x_w$ of the real plant in the actual state in response to the difference signal input (r−y). The trajectory compensation signal u' is the control input that compensates for the trajectory following error of the needle robot 31 corresponding to the position of the puncture needle 21.

The displacement compensation block 8 determines initial control parameters based on the organ model 22 representing the characteristics of the organ. When the signal of the position $y_o$ of the puncture needle 21 is input to the displacement compensation block 8, the displacement compensation block 8 generates and outputs a portion compensation signal u" so that the puncture needle minimizes the displacement of the puncture target position in the organ. In the displacement compensation block 8, control parameters of the displacement compensation block 8 are revised so that the state $x_w$ of the real plant represents the actual characteristics of the organ in the state in which the puncture needle 21 is traveling through the organ. The displacement compensation block 8 having the revised control parameters generates and outputs the portion compensation signal u" corresponding to the displaced position of the puncture target position in the organ so as to suit the state $x_w$ of the real plant in the actual state in response to the signal of the position $y_o$.

The adder 13 adds the output u' of the trajectory error compensation block 7 and the output u" of the displacement compensation block 8 to output the control input u. Based on the control input u, the actuator of the needle robot 31 is driven so as to control the position of the puncture needle 21. Then, the puncture needle travels with the control forces and the control torque corresponding to the control input u to change the position of the target position. The position of the target position is obtained as the state $x_w$ of the real plant by the image obtaining unit 33. Based on the state $x_w$ of the real plant, the control parameters (of the organ model 22) of the displacement compensation block 8 are revised so as to represent the actual characteristics of the organ in the state in which the puncture needle 21 is traveling through the organ.

The trajectory error compensation block 7 and the displacement compensation block 8 are provided in the calculation unit 3 of the puncture control system 1 as a trajectory error compensation filter 7 and a displacement compensation filter 8, respectively.

The trajectory compensation signal u', the portion compensation signal u", and the added signal u are expressed as vector quantities having $u'=[f_x', f_y', t_\theta']^T$, $u''=[f_x'', f_y'', t_\theta'']^T$, $u=[f_x, f_y, t_\theta]^T$ as their components, respectively. In practice, the components of the control input vectors u' and u" are output depending on the state of the needle robot 31 and the state of the organ model 22. For simplification, only a control torque $t_\theta$ is described here, but the same is applied to the control forces $f_x$ and $f_y$ which are the other components applied to the puncture needle 21.

Figure 6A:
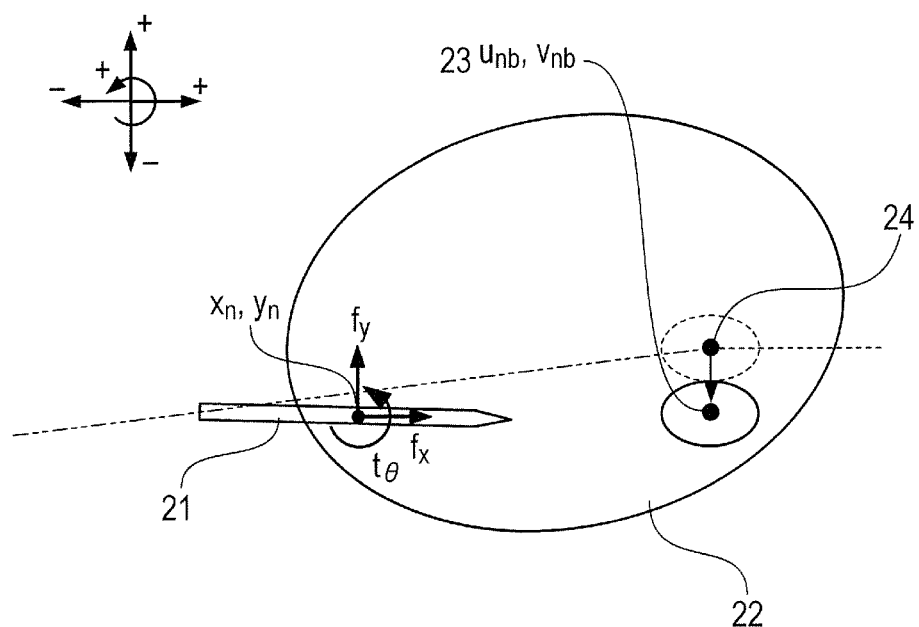
FIGS. 6A and 6B are explanatory diagrams for illustrating relationships between trajectories of the puncture needle and positions of a puncture target position according to the present invention.

As illustrated in FIG. 6A, a case where a puncture error due to the resistance of the organ causes the tip of the puncture needle 21 of the needle robot 31 to be deviated from the trajectory in a negative direction of a y coordinate and the position 24 of the puncture target position is moved to the position 23 in the negative direction of the y coordinate is taken as an example. In this case, the trajectory error compensation filter 7 outputs a positive value as a control torque $t_\theta'$ so as to make the needle robot follow the trajectory. Moreover, the displacement compensation filter 8 functions so as to reduce the shift of the puncture target position to 0 by the control input to the needle robot 31, and hence outputs a positive value as a control torque $t_\theta''$. The two signals are added by the adder 13, and hence the input signal is generated so that the displacement of the puncture target position is minimized by the displacement compensation filter 8 having the revised control parameters. In this manner, trajectory control of the needle robot as well as control to minimize the displacement of the puncture target position is realized.

Figure 6B:
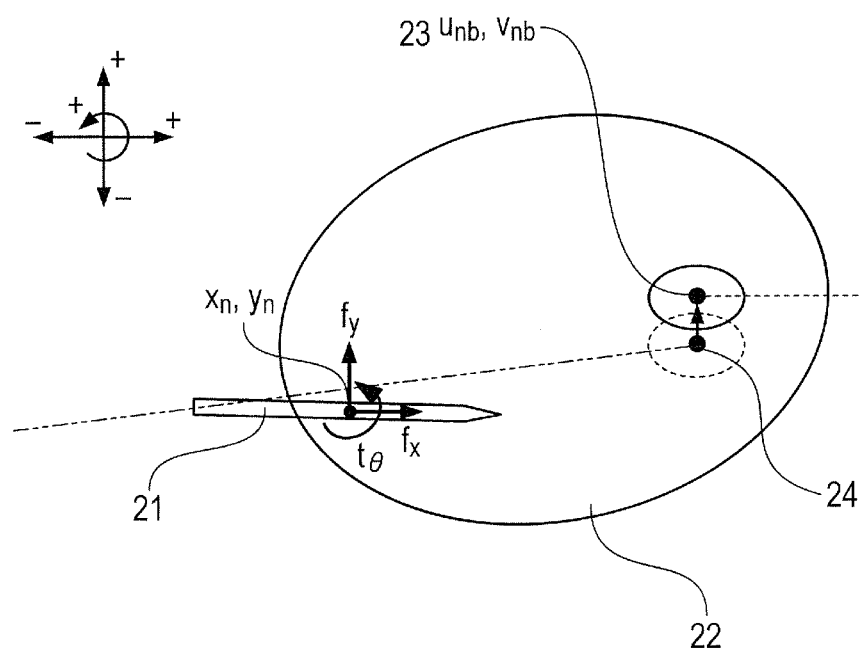

Next, as illustrated in FIG. 6B, a case where the tip of the puncture needle 21 of the needle robot 31 is deviated from the trajectory in the negative direction of the y coordinate and the shift of the puncture target position is moved in a positive direction of the y coordinate is taken as an example. In this case, the trajectory error compensation filter 7 outputs a positive value as the control torque $t_\theta'$ so as to make the needle robot follow the trajectory. The displacement compensation filter 8 functions so as to reduce the shift of the puncture target position to 0 by the control input to the needle robot, and hence outputs a negative value as the control torque $t_\theta''$.

The control parameters of the displacement compensation filter 8 are changed by the organ model 22 to generate the input $u''=[f_x'' f_y'' t_\theta'']^T$ that moves the shift of the puncture target position to a direction opposite to the direction of movement of the target position.

Those two signals $t_\theta'$ and $t_\theta''$ are added by the adder 13, with the result that the control torque $t_\theta$ for driving the needle robot 31 becomes a value smaller than $t_\theta'$ that takes driving of the needle robot alone into consideration. In other words, the input $u''=[f_x'' f_y'' t_\theta'']^T$ for moving the shift of the puncture target position in such a direction as to maintain the initial position as much as possible is generated.

As a result, an operation in which the needle robot gradually recovers to the trajectory while minimizing the displacement of the puncture target position is realized. In other words, at a position where the effects of the control torque $t_\theta$ on the puncture target position are reduced, the puncture needle quickly recovers to the trajectory. When the recovery to the trajectory is too gradual, the weighting functions $W_{s1}$ and $W_{s2}$ may be adjusted based on numerical simulation.

In FIGS. 6A and 6B, the cases where the tip of the puncture needle 21 of the needle robot 31 is deviated from the trajectory in the negative direction of the y coordinate have been described, but the same applies to a case where the tip of the puncture needle 21 of the needle robot 31 is deviated from the trajectory in the positive direction of the y coordinate. In this case, the sign of the value of $t_\theta''$ described above may be inverted.

Figure 7:
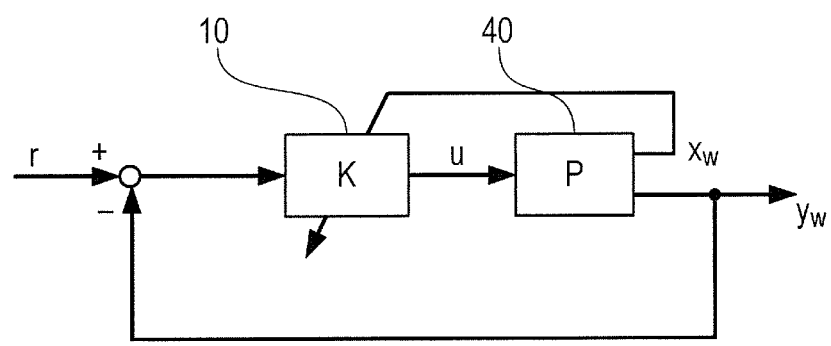
FIG. 7 is a block diagram illustrating the entire control system according to the present invention.

FIG. 7 is a block diagram of a case where a real plant 40 of the puncture system is applied to the control system of the extended system 25. In this case, the real plant 40 corresponds to the extended system 25 expressed by Equation (8), and is a time-variant system in which a system matrix and a control input matrix vary depending on the state.

The control input u output from the control system 10 illustrated in FIG. 5 is input to the real plant 40. The control input u is input to the manipulator 32, which is the real plant, and output as the control forces and the control torque for the puncture needle 21. The puncture needle 21 controlled by the control forces and the control torque deforms the organ, which leads to a change in characteristics of the organ, such as a displacement of the target position. The characteristics are obtained as the state by the image obtaining unit 33. The obtained state is input to the trajectory error compensation filter 7 and the displacement compensation filter 8. The control parameters of each of the trajectory error compensation filter 7 and the displacement compensation filter 8 are revised by the input state. Based on the state of the organ that changes with the travel of the puncture needle 21, the control parameters of each of the trajectory error compensation filter 7 and the displacement compensation filter 8 are sequentially revised in time series. In other words, the control parameters are revised based on the changing state of the organ, and hence the added signal u becomes an input signal that minimizes the displacement of the target position to be punctured and causes the puncture needle 21 to gradually recover to the trajectory.

Further, the filters of the weighting functions in the paths of the control amounts $z_{21}$ and $z_{22}$ illustrated in the plant model of FIG. 4 may be added to an output line of the real plant 40 of FIG. 7. Those filters multiply the output of the state defined by the information on the position of the puncture needle 21, which is obtained by the detector 34, and the information on the organ, which is obtained as an image by the image obtaining unit 33, by the weighting functions. In this manner, in revising the control parameters of each of the trajectory error compensation filter 7 and the displacement compensation filter 8, the effects of the control forces and the control torque imparted to the puncture needle 21 may be changed.

3) Control Sequence of Puncture Control System

Figure 8:
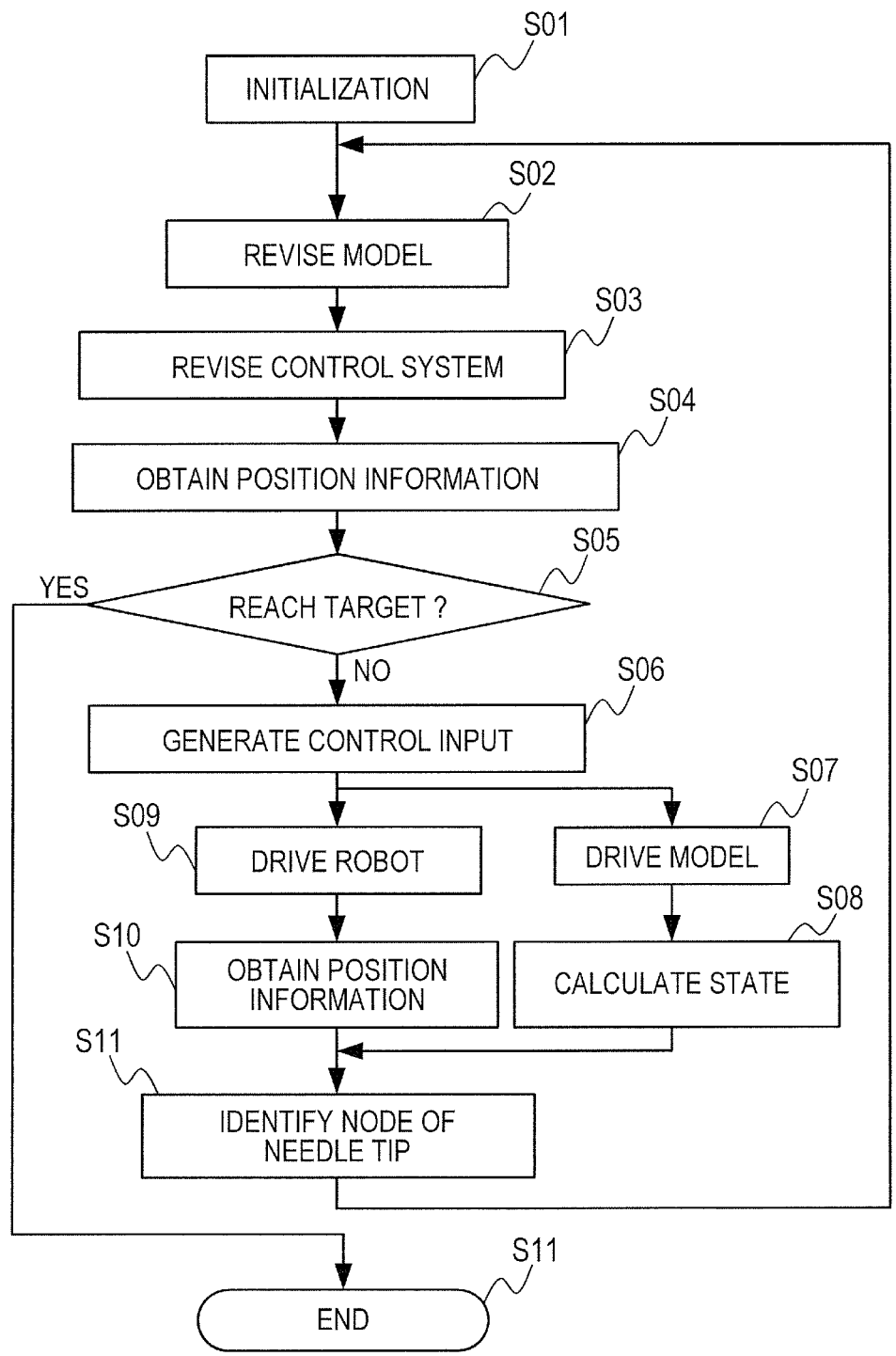
FIG. 8 is a flowchart illustrating a control sequence according to the present invention.

The H∞ control theory does not compensate for the control performance of the time-variant system. Therefore, the puncture control is performed using a control sequence illustrated in FIG. 8. Steps of the control sequence are described below.

1. A trajectory that connects the puncture target position and a puncture portion is generated (S01).
2. The tip of the puncture needle 21 of the needle robot is moved to the ne-th node $(u_{ne}, v_{ne})$ corresponding to the puncture portion of the organ model 22 (S01).
3. The nt-th node to which the forces of the needle robot are applied is set to the ne-th node (S01). The state $x_w$ of the extended system is initialized (S01). The displacement compensation filter 8 determines initial control parameters so as to correspond to the organ model 22.
4. The extended system model of Equation (8) is derived. In order to derive the control system, the extended system model is revised (S02). In the revision, order reduction is performed by a modal truncation method or the like.
5. The control system based on the evaluation function of Equation (10) is derived (S03).
6. A shift y of the puncture needle 21 of the needle robot and a shift $y_o$ of the puncture target position of the organ are obtained using the angle sensor, an image, and the like (S04).
7. When the tip of the puncture needle 21 of the needle robot has reached the target position of the organ, the control sequence is ended, and when the tip of the puncture needle 21 of the needle robot has not reached the target position, the steps are continuously performed (S05).
8. The control input u is generated using displacement information y and $y_o$ and Equation (12) (S06).
9. The control input u is applied to the extended system (S07), and the state $x_w$ is calculated (S08).
10. The control input u is applied to drive the needle robot 31 for a period of sampling time Δt (S09). The displacement information of the target position, which is displaced with the travel of the puncture needle 21 through the organ, is obtained by an image obtaining device (S10). Moreover, the information on the position of the tip portion of the puncture needle 21 is obtained by the detector (S10).
11. A stress and the like of the tip portion of the puncture needle of the needle robot are calculated or at the same time pieces of the displacement information of the model are compared by using the extended system model to identify which node of the organ model 22 the displacement of the tip of the needle robot corresponds to (S11).
12. The sequence returns to the step of revising the extended system model (S02).

In summary, the organ puncture system according to the present invention operates as follows.

Figure 9A:
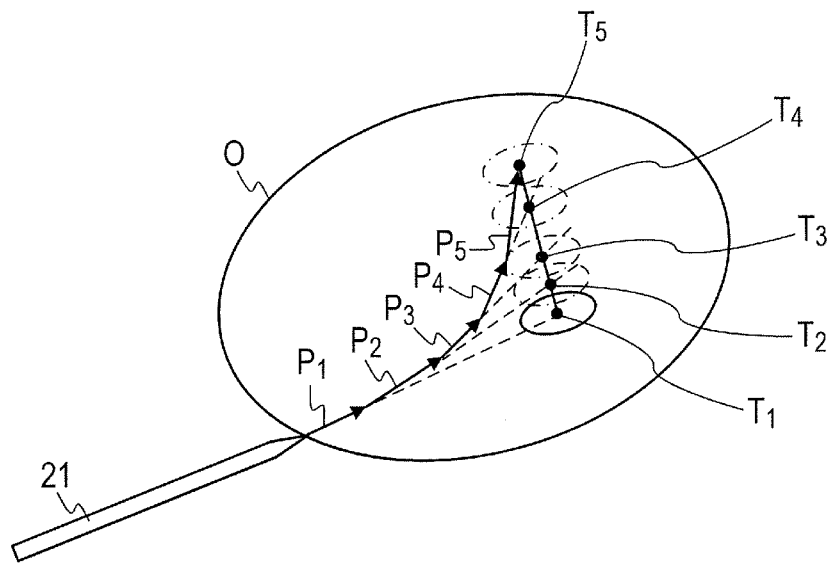
FIG. 9A is a conceptual diagram illustrating, based on the disclosure of PTL 1, a travel route of a puncture needle and how a target position of an organ moves.
Figure 9B:
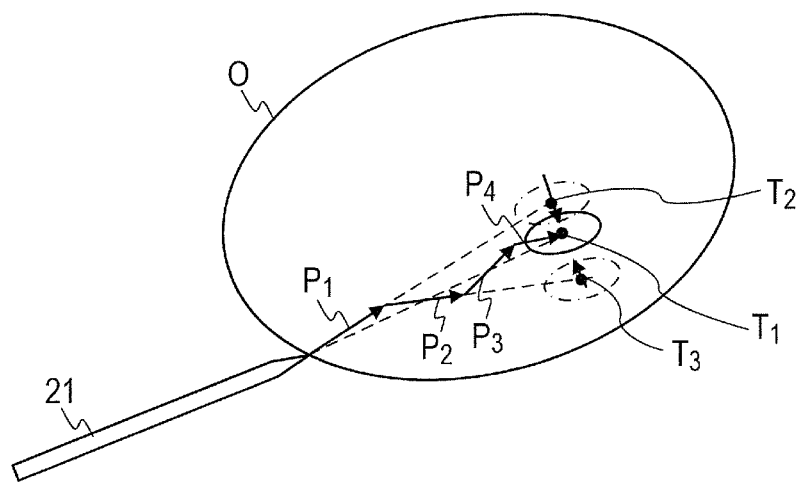
FIG. 9B is a conceptual diagram illustrating, in a puncture control system to which the present invention is applied, a travel route of the puncture needle and how the target position of the organ moves.

As illustrated in FIG. 9B, first, the puncture needle 21 is inserted to the organ O and toward the position T1 of the target position obtained in the state before the puncture needle 21 enters into the organ. When the puncture needle 21 is inserted to and travels through the organ (P1), it is expected that the organ is deformed by the force imparted to the outer wall of the organ at the time of insertion and the force with which the puncture needle 21 travels through the organ, so that the position T1 of the target position is displaced to the position T2. The shifts are predicted, the organ model 22 is revised based on the state variables in the subsequent real control step, and the output of the organ model 22 is used to change a course toward the target position T2 in the expected direction of movement to P2. In this manner, the target position is displaced to return to the T1 side.

Further, on the other hand, when the shifts are beyond the initial target position T1, for example, the course toward the target position T3 in the expected direction of movement is changed to P3 so that the target position is displaced to return to the T1 side.

In other words, the organ puncture system sequentially determines a direction of travel of the puncture needle 21 so as to cause a minimum displacement that allows the target position to maintain the initial position.

Advantageous Effects of Invention

According to the present invention, the puncture needle may accurately reach the target position while minimizing the displacement of the puncture target position. Therefore, a medical robot system for performing punctuation with high accuracy without damaging normal tissues is provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-142961, filed Jun. 26, 2012, which is hereby incorporated by reference herein in its entirety.

The invention claimed is:

1. A puncture control system for controlling an organ puncture system having a puncture needle, a detector for obtaining information on a position of the puncture needle, and a target position obtaining unit for obtaining information on the target position, the puncture control system comprising:
    a trajectory error compensation unit that outputs a signal for compensating for a displacement of the puncture needle from a target trajectory, based on the information on the position of the puncture needle obtained by the detector;
    a displacement compensation unit whose initial control parameters are determined so as to correspond to a model representing characteristics of the organ, the displacement compensation unit outputting a displacement compensation signal for minimizing the displacement of the target position; and
    an adder that outputs a signal obtained by adding the signal output by the trajectory error compensation unit and the displacement compensation signal,
    wherein a control force and a control torque of the puncture needle is determined based on the signal output from the adder, and
    wherein control parameters of each of the trajectory error compensation unit and the displacement compensation unit are revised based on the state of the organ obtained by the target position obtaining unit.

2. The puncture control system according to claim 1, further comprising a multiplying unit that multiplies the information of the position of the puncture needle, which is obtained by the detector, and the state of the organ, which is obtained by the target position obtaining unit, by weighting functions.

3. The puncture control system according to claim 1, wherein the characteristics of the organ include stiffness, mass, and an attenuation amount of a force that has acted on the organ.

4. An organ puncture system, comprising:
    a puncture needle;
    a manipulator that controls a control force and a control torque applied to the puncture needle to move the puncture needle toward a target position within an organ;
    a detector that obtains information of a position of the puncture needle;
    a target position obtaining unit that obtains information on the target position;
    a trajectory error compensation that outputs a signal for compensating for a displacement of the puncture needle from a target trajectory, based on the information on the position of the puncture needle obtained by the detector;
    a displacement compensation unit whose initial control parameters are determined so as to correspond to a model representing characteristics of the organ, the displacement compensation unit outputting a displacement compensation signal for minimizing the displacement of the target position; and
    an adder that outputs a signal obtained by adding the signal output by the trajectory error compensation unit and the displacement compensation signal,
    wherein the control force and the control torque of the puncture needle is determined based on the signal output by the adder, and
    wherein control parameters of each of the trajectory error compensation unit and the displacement compensation unit are revised based on the state of the organ obtained by the target position obtaining unit.

5. A puncture control method for controlling a position of a puncture needle that moves toward a target position of an organ, the puncture needle changing a state of the organ with travel through the organ, wherein the puncture control method comprises
    sequentially determining a direction of travel of the puncture needle according to the travel of the puncture needle so as to minimize a displacement of the target position; and
    controlling, with an added signal obtained by adding a trajectory compensation signal for compensating for a displacement of the puncture needle from a target trajectory based on the information on the position of the puncture needle and a portion compensation signal for minimizing the displacement of the target position, a control force and a control torque to be imparted to the puncture needle,
    wherein control parameters for generating each of the trajectory compensation signal and the portion compensation signal are revised based on a state of the organ.

6. The puncture control system according to claim 2, wherein the characteristics of the organ include stiffness, mass, and an attenuation amount of a force that has acted on the organ.

7. An organ puncture system according to claim 4, further comprising:
    a multiplying unit that multiplies the information of the position of the puncture needle, which is obtained by the detector, and the state of the organ, which is obtained by the target position obtaining unit, by weighting functions.

8. A puncture control system comprising:
    a puncture needle configured to puncture an organ; and
    a controller configured to control the puncture needle to reach a target position of the organ, such that a trajectory of the puncture needle follows a path in which a displacement of a target position due to a movement of the puncture needle within the organ is minimized.

9. The puncture control system according to claim 8, wherein the controller further calculates the trajectory to be followed by the puncture needle.

10. The puncture control system according to claim 9, further comprising an image obtaining unit,
    wherein the controller calculates the trajectory on the basis of a shift of the target position obtained from an image obtained by the image obtaining unit.

11. The puncture control system according to claim 8, further comprising a manipulator configured to drive the puncture needle.

12. The puncture control system according to claim 1, wherein the target position obtaining unit comprises an image obtaining unit that obtains an image, and wherein the information on the target position is obtained using the image.

13. The organ puncture system according to claim 4, wherein the target position obtaining unit comprises an image obtaining unit that obtains an image, and wherein the information on the target position is obtained using the image.

14. A puncture control system for controlling a puncture needle, the puncture control system comprising:
   a controller configured to control the puncture needle to reach a target position of an organ, such that the puncture needle follows a path in which a displacement of a target position due to a movement of the puncture needle within the organ is reduced.

15. The puncture control system according to claim 14, wherein the controller further calculates a trajectory to be followed by the puncture needle.

16. The puncture control system according to claim 15, wherein the controller calculates the trajectory on the basis of a shift of the target position obtained from an image obtained by an image obtaining unit.

17. The puncture control system according to claim 14, wherein the controller controls the movement of the puncture needle by controlling control force and control torque applied to the puncture needle.

18. The puncture control system according to claim 17, wherein the controller revises the control force and the control torque after the puncture needle proceeds a predetermined distance.

* * * * *